United States Patent [19]

Edwards et al.

[11] Patent Number: 5,787,889
[45] Date of Patent: Aug. 4, 1998

[54] ULTRASOUND IMAGING WITH REAL TIME 3D IMAGE RECONSTRUCTION AND VISUALIZATION

[75] Inventors: Warren Edwards; Christian Deforge; Yongmin Kim, all of Seattle, Wash.

[73] Assignee: University of Washington, Seattle, Wash.

[21] Appl. No.: 804,054

[22] Filed: Feb. 21, 1997

Related U.S. Application Data

[60] Provisional application No. 60/033,520 Dec. 18, 1996.

[51] Int. Cl.$^6$ .................................................. A61B 8/00
[52] U.S. Cl. .................................. 128/660.07; 128/916
[58] Field of Search ........................ 128/660.04–660.05, 128/660.07, 661.01, 916; 395/119; 382/128, 285

[56] References Cited

U.S. PATENT DOCUMENTS

| | | | |
|---|---|---|---|
| 5,396,890 | 3/1995 | Weng | 128/916 X |
| 5,454,371 | 10/1995 | Fevater et al. | 128/660.07 |
| 5,485,842 | 1/1996 | Quistgaard | 128/660.07 |
| 5,492,125 | 2/1996 | Kim et al. | |
| 5,529,070 | 6/1996 | Augustine et al. | 128/916 X |
| 5,582,173 | 12/1996 | Li | 128/660.07 |

OTHER PUBLICATIONS

Axel et al., "Three–Dimensional Display of Nuclear MAgnetic Resonance, (NMR) Cardiovascular Images," Journal of Computer Assisted Tomography vol. 7, No. 1, 1983.

Valentino et al., Volume Rendering of Multimodal Images: Application to MRI and PET Imaging of the Human Brain,: IEEE Transactions on Medical Imaging; vol. 10, No. 4, 1991.

Levoy, Marc; "Volume Rendering Display of Surfaces from Volume Data," IEEE Computer Graphics and Applications; May 1988.

Lacroute et al., "Fast Volume Rendering using a Shear–Warp Factorization of the Viewing Transformation," Computer Graphics Proceedings 1994.

Ritchie et al., "Three–Dimensional Ultrasonic Angiography Using Power Mode Doppler," Ultrasound in Med. & Biol., vol. 22, No. 3; 1996.

Schreiner et al., "A Fast Maximum–Intensity Projection Algorithm for Generating Magnetic Resonance Angiograms," IEEE Transactions on Medical Imaging, vol. 12, No. 1 Mar. 1993.

Zuiderveld et al., "Techniques for Speeding Up Hig–Quality Perspective Maximum Intensity Projection," Pattern Recognition Letters 15; 1994.

Ericke et al., "Visualization of Vasculature From Volume Data," Comput. & Graphics, vol. 18, No. 3, 1994.

(List continued on next page.)

*Primary Examiner*—Francis Jaworski
*Attorney, Agent, or Firm*—Steven P. Koda

[57] ABSTRACT

A 3D image is generated in real-time on an ultrasound medical imaging system which performs acquisition, volume reconstruction, and image visualization tasks using multiple processors. The acquisition task includes deriving position and orientation indicators for each gathered image frame. Volume reconstruction includes defining a reference coordinate system within which each image frame in a sequence of image frames is registered. The reference coordinate system is the coordinate system for a 3D volume encompassing the image planes to be used in the 3D image. The first image frame is used to define the reference coordinate system. As each image plane is registered, a 2D projection of the incremental volume is displayed. A shear-warp factorization process is used to derive a 2D projection for a rotated volume. A viewing transformation matrix is factorized into a 3D shear which is parallel to slices of the reference volume. A 2D warp then is implemented to produce the projection of the rotated volume.

23 Claims, 7 Drawing Sheets

OTHER PUBLICATIONS

Ohbuchi et al., "Incremental Volume Rendering Algorithm for Interactive 3D Ultrasound Imaging," Proceedings of the 12th Int'l Conf. on Information Processing in Medical Imaging, pp. 486–500; 1991.

State et al., "CaseStudy: Observing a Volume Rendered Fetus within a Pregnant Patient," IEEE Comput. Proceeding Visualization, pp. 364–368; 1994.

Crass et al., "Radiological Application of Three-Dimensional Imaging System," Seminars in Ultrasouns, CT, and MRI vol. 13, No. 2; pp. 94–101, Apr. 1992.

Nelson et al., "Visualization of 3d Ultrasound Data," IEEE Computer Graphics & Applications; Nov. 1993.

Lacroute et al., "Real–Time Volume Rendering on Shared Memory Multiprocessors Using the Shear–Warp Factorization," Proceedings of Parallel Rendering Symposium, pp. 15–22, 1995.

(Si >= 0, Sj >=0) => (Ti = 0, Tj = 0)

(Si < 0, Sj >= 0) => (Ti = -Si•DEPTH, Tj = 0)

$(Si >= 0, Sj < 0) \Rightarrow (Ti = 0, Tj = -Sj \cdot Depth)$ $(Si < 0, Sj < 0) \Rightarrow (Ti = -Si \cdot Depth, Tj = -Sj \cdot Depth)$

ULTRASOUND IMAGING WITH REAL TIME 3D IMAGE RECONSTRUCTION AND VISUALIZATION

CROSS REFERENCE TO RELATED APPLICATION

This application is related to U.S. Provisional Patent Application Ser. No. 60/033,520 filed Dec. 18, 1996 for Real Time 3D Ultrasound.

BACKGROUND OF THE INVENTION

This invention relates to ultrasound imaging systems, and more particularly to generation and visualization of three dimensional ultrasound images.

Medical imaging systems are used as diagnostic tools for viewing internal areas of a patient's body. Imaging systems based on ultrasound technology are desirable because such systems are non-invasive, portable and generally easy to use. Ultrasound energy is sound wave energy having a frequency greater than approximately 20 kHz. To generate ultrasound energy, electronic signals are input to a transducer which converts the electrical signals into ultrasound signals. Ultrasound signals, typically of 2 MHz to 10 MHz, are transmitted into a patient's body where they are in-part absorbed, dispersed, refracted and reflected. Reflected ultrasound signals are received at transducer elements which convert the reflected ultrasound signals back into electronic echo signals. The echo signals undergo beamforming to correlate the ultrasound signals. Subsequently the beam-formed signals are processed to analyze echo, Doppler, and flow information and obtain an image of the patient's targeted anatomy (e.g., tissue, fetus, vessels).

A B-mode image, for example, is a brightness image in which component pixels are brightened in proportion to a corresponding echo signal strength. The brightness image represents a two dimensional cross section of a patient target area through a transducer's scanning plane. Typically the B-mode image is a gray scale image in which the range of darker to brighter gray-scale shades corresponds to increasing brightness or echo strength. The typical ultrasound B-mode image is formed by a linear scan or sector scan of the patient's target area by the transducer probe. The individual images produced by ultrasound imaging systems include discrete frames. Each frame has a limited field of view due to a relatively narrow region traversed by the transmitted ultrasound energy. As the transducer probe is manipulated along the patient's body surface, each previous image is replaced on the viewing display by a new image defined by the current position, and thus field of view, of the transducer probe.

Conventionally, ultrasound has been used for generating two dimensional images. Large amounts of data and complex analysis of the data initially drove ultrasound systems to be hardwired boards of dedicated subsystems doing specific ultrasound tasks (such as echo processing, scan conversion or Doppler processing). The advent of faster processors and distributed processing has led to use of programmable processor boards to perform one or more tasks previously performed using dedicated hardwired subsystems. This invention is directed to image processing tasks, and more particularly to methods for achieving and visualizing three dimensional ultrasound images in real-time with an ultrasound medical imaging system. A three dimensional (3D) image as used herein refers to an image on a two dimensional display giving the viewer a three dimensional impression.

SUMMARY OF THE INVENTION

According to the invention, 3D image generation includes data acquisition, volume reconstruction, and image visualization. This invention is directed toward volume reconstruction and image visualization processes and works with data derived from a data acquisition process. Data acquisition includes receiving multiple frames of data while scanning a patient's target anatomy with a transducer probe. The acquisition task includes deriving position and orientation indicators for each frame relative to a prior frame, a reference frame or a reference position. The frame data and corresponding indicators for each frame are input to the volume reconstruction and image visualization processes.

According to one aspect of the invention, volume reconstruction is performed by defining a reference coordinate system within which each image frame in a sequence of image frames is registered. The reference coordinate system is the coordinate system for a 3D volume encompassing all image planes to be used in generating a 3D image. The first image frame is used to define the reference coordinate system (and thus the 3D volume). The reference coordinate system has three orthogonal axes (i.e., $x_r$, $y_r$, and $z_r$ axes). Each image frame is a 2D slice having two orthogonal axes (i.e., $x_i$ and $y_i$ where i is the i-th image frame). Because the ultrasound probe may move among various degrees of freedom, image frames after the first image frame need not define parallel planes within the reference coordinate system. The first image frame occurs at a plane $z_r=0$ of the reference coordinate system. The $x_1$ axis is parallel to the $x_r$ axis. The $y_1$ axis is parallel to $y_r$ axis. Typically $x_1=x_r+k$, where k is a constant; and $y_1=y_r+m$, where m is a constant. In one embodiment the 3D reference volume occurs in the first quadrant of the reference coordinate system.

According to another aspect of the invention, the sequence of image frames are registered in the reference coordinate system using the position and orientation indicators for each respective frame. For any given image frame, the ultrasound data represents sample points within a two dimensional image plane. Each image plane has an image plane coordinate system defined by two axes (i.e., $x_i$ and $y_i$ where i is the i-th image frame). The image planes and thus the coordinate systems need not be parallel for the respective image planes. Each sample point within an image plane has image plane coordinates in the image plane coordinate system for such image plane. To register the samples in the reference coordinate system, the sample point coordinates in the appropriate image plane coordinate system are transposed to the reference coordinate system. Where for example, an image plane sample does not occur at specific integer coordinates of the reference coordinate system, interpolation is used to distribute the image plane sample among the nearest reference coordinate system points. In one embodiment the sample data is distributed into a cube surrounding the sample, where the vertices of the cube are 8 points of the reference coordinate system nearest to the sample position. In some embodiments, to compensate for under-sampling the image plane sample is allocated among more than just the 8 nearest reference plane coordinate points (i.e., voxels). Where the image plane sample does not transpose within the 3D reference volume the sample is ignored—for purposes of volume reconstruction and visualization.

According to another aspect of the invention, memory address space is allocated to store sample data or the interpolated values derived from the sample data. The memory is mapped to the reference coordinate system. Thus, values for a given row of a given reference volume slice (taken along for example the z-axis) are stored in sequential address locations. Also, values for adjacent rows in such slice are stored in adjacent first memory address space.

According to another aspect of this invention, as each subsequent image plane is registered in the reference coordinate system it is displayed with the prior image planes using an image visualization process. The operator can view the 3 dimensional image in real time as it is being constructed from the 2 dimensional image planes. In one embodiment an orthogonally rendered 2D projection of the volume under construction is displayed. Because the projection is an orthogonal projection, further interpolation is not needed to project the incrementally constructed volume onto the viewing plane. As image planes are registered into the 3D volume and projected onto the viewing plane, portions of respective image planes overlap (due to the perspective viewing angle). According to a maximum intensity projection (MIP') visualization technique, when a pixel of the viewing plane projection corresponds to values from multiple image planes, the value corresponding to the greatest intensity among the values for the respective image planes is used for the pixel.

Once a 3D image is captured, reconstructed and initially displayed, the operator then can perform various visualization tasks on the image in real time. Specifically, the operator can rotate the 3D image or jump to different viewing angles of the 3D image. A fast process for rendering volumes called shear-warp factorization is used to derive each 2D projection data frame of the rotating or rotated image. The process factorizes a viewing transformation matrix into a 3D shear which is parallel to slices of the reference volume. A projection of the shear forms a 2D intermediate image. A 2D warp then is implemented to produce the final image, (i.e., a 2D projection of the 3D volume at a desired viewing angle). The process is allocated among multiprocessors which process blocks of image data. The blocks are processed by performing computations on image data in the order stored in memory. This results in an efficient visualization scheme.

These and other aspects of the invention will be better understood by reference to the following detailed description taken in conjunction with the accompanying drawings.

DESCRIPTION OF SPECIFIC EMBODIMENTS

Exemplary Host Platform

Figure 1:
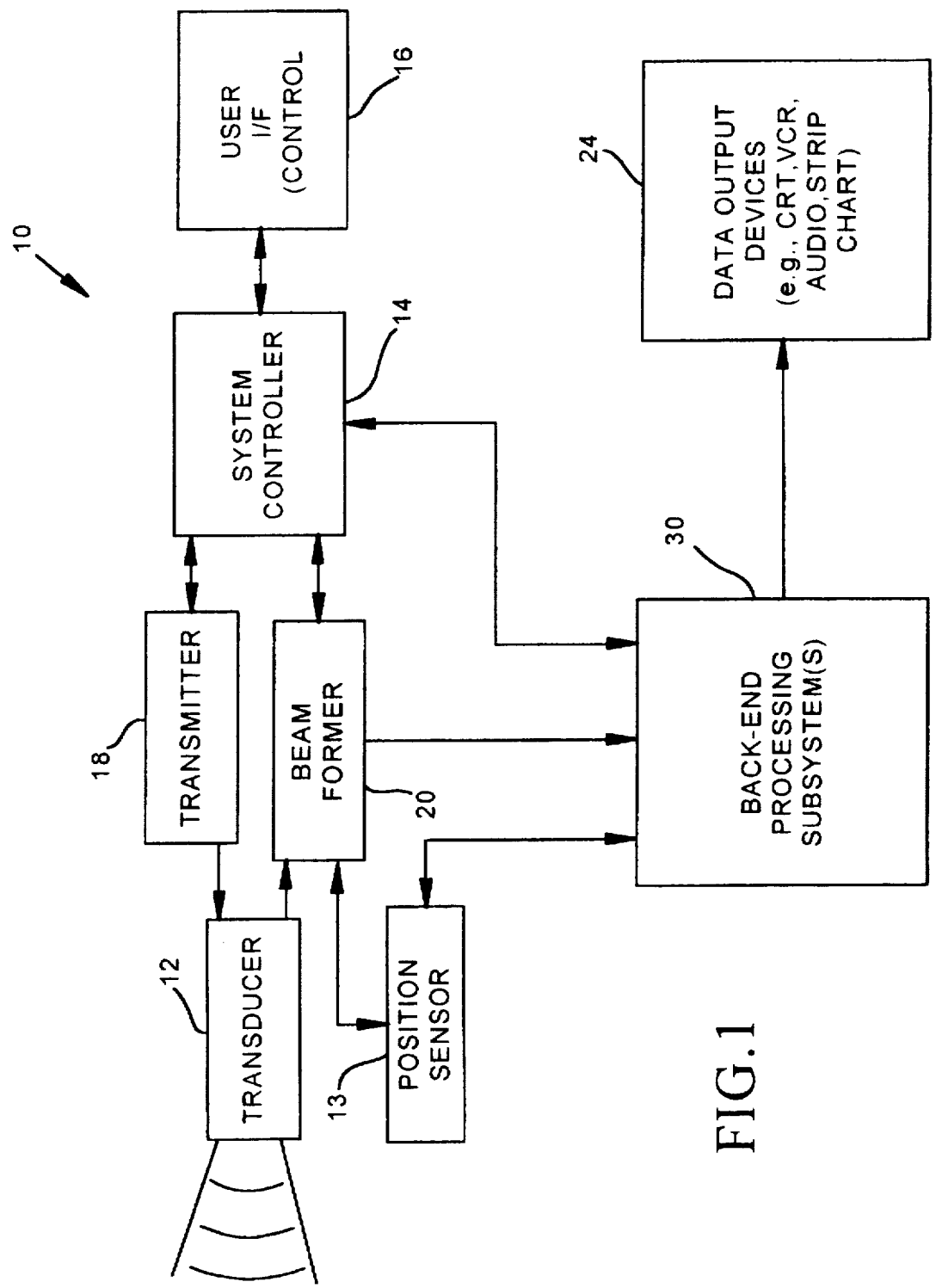
FIG. 1 is a block diagram of an ultrasound medical diagnostic imaging system.

FIG. 1 shows a block diagram of a host ultrasound medical diagnostic imaging system 10 for implementing a method embodiment of this invention. The function of the system 10 is to perform diagnostic imaging of a patient using ultrasound data. Ultrasound signals are transmitted via a transducer 12 into a patient. Reflected signals are detected and used to derive internal images of the patient for a scanned area/volume.

A system controller 14 receives and displays user control information via a user interface 16. During operation, system control signals are output to an ultrasound front end (i.e., transducer 12, a transmitter 18, a beam-former 20, and related circuitry) and to various subsystems. Transmitter 18 generates output signals to transducer 12 to define aperture, apodization, focus, and steering of ultrasound signals. Transducer 12 is an array of transducer elements. The elements define multiple channels, each channel for transmitting and/or receiving ultrasound signals. Transmitted ultrasound signals are in part absorbed, dispersed, refracted, and reflected when travelling through a patient. Reflected signals are sensed by transducer 12 and captured as a patterned beam by beam-former 20. The captured signals are sent to one or more back-end processing subsystems 30. The function of the back-end processing subsystem(s) 30 is to process the raw beam data and generate image data for output devices 24. In some embodiments the front end also includes a position sensor 13 to derive the position and orientation of the transducer at any instance in time.

Figure 2:
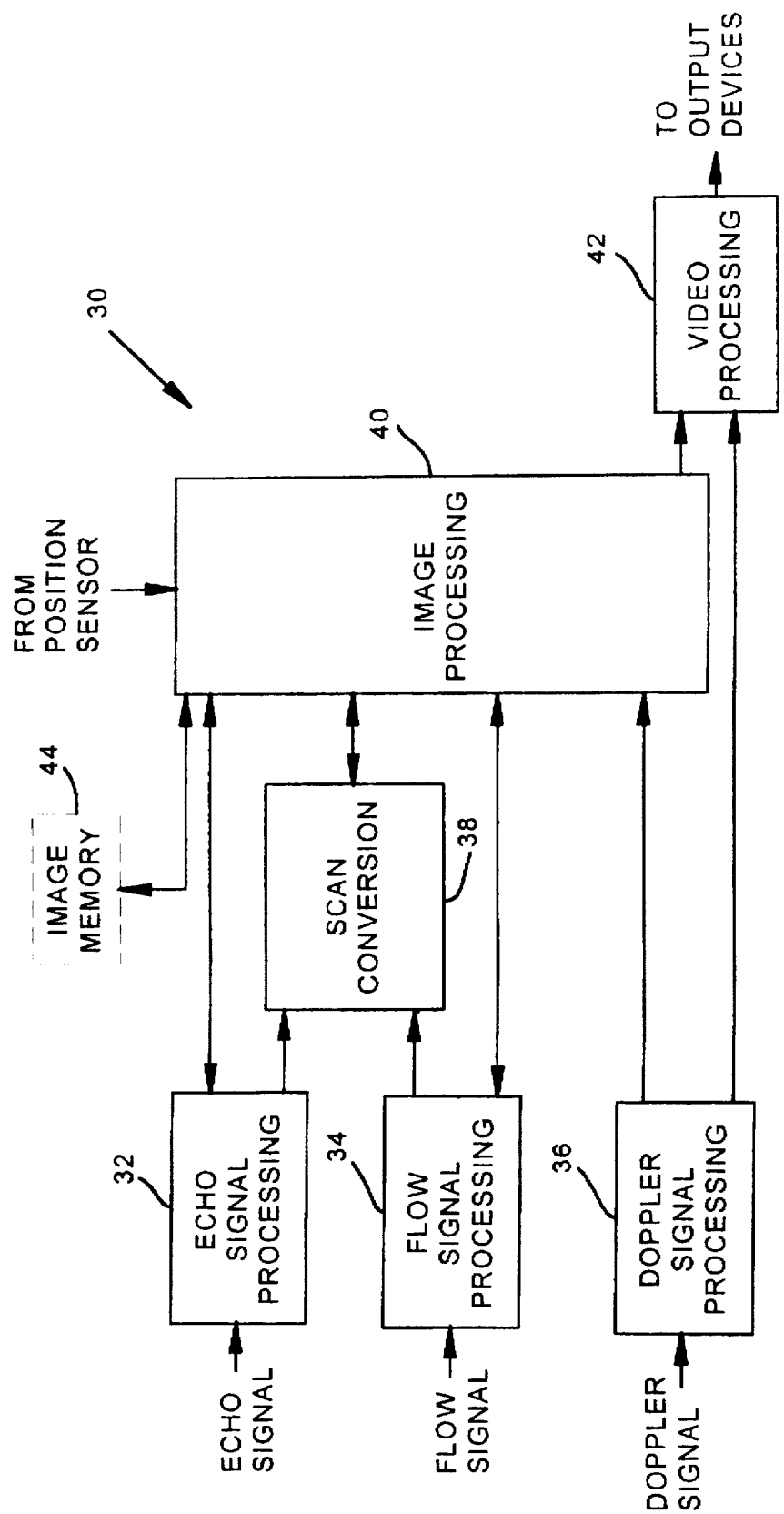
FIG. 2 is a control flow diagram of back-end processing tasks.

FIG. 2 is a block diagram of back-end processing tasks 32-42. Digital echo signals, flow signals, and/or Doppler signals are received at the back-end processing subsystem(s) 30 according to various modes of operation. In one embodiment there is a hardwired subsystem for each of the back-end processing tasks 32-42. In another embodiment there are one or more processor boards respectively programmed to perform one or more of the tasks 32-42. In a preferred embodiment the back-end processing subsystem(s) 30 are implemented with at least one programmable processor board to perform one or more tasks 32-42, and 0 or more dedicated boards to perform, respectively, 0 or more of the remaining tasks 32-42.

The input signals received at the back-end subsystem(s) 30 are referred to herein as vector signals. For a transducer 12 performing sector scanning, the vector signals are digital polar-coordinate data samples of echo, flow, and/or Doppler signals. For a transducer 12 performing linear scanning, the vector signals are digital cartesian-coordinate data samples of echo, flow, and/or Doppler signals.

The back-end processing tasks include echo signal processing 32, flow signal processing 34, Doppler signal processing 36, scan conversion 38, image processing 40, and video processing 42. Echo signal processing 32 typically encompasses signal enhancement filtering, energy detection, and image enhancement filtering. Various filtering and convolution techniques are employed. The purpose of echo signal processing 32 is to enhance the signal-to-noise ratio of the echo signal. Flow signal processing 34 analyzes signals for flow parameters. Typical parameter derivations include sample correlation and flow averaging. The purpose of flow signal processing 34 is to identify flow and turbulence within a scanned area. Doppler signal processing 36 typically encompasses signal enhancement filtering, spectral estimation processing, energy detection, and derived waveform filtering. The purpose of Doppler signal processing 36 is to identify and filter out Doppler shift, to improve spectral frequency response and to coordinate spectral mapping.

A scan conversion process 38 converts the processed vector data streams from echo signal processing 32 and flow signal processing 34. For polar-coordinate vector data, the data is converted into cartesian-coordinate raster data. For cartesian-coordinate vector data, the data is scaled into cartesian-coordinate raster data.

Image processing 40 includes image enhancement and processing executed on the raster data or vector data. In an off-line delayed playback (e.g., cine playback) mode of operation image data, vector data and/or raster data is received from image memory 44 and processed. Image processing 40 includes the volume reconstruction and image visualization methods discussed in detail below.

Video processing 42 executes on the image processed data to generate video signals, audio signals, and graphing signals for output to a display device, audio device, storage device (e.g., VCR), and/or charting device. Video processing 42 in some applications also executes on Doppler processed vector data to generate similar video signals, audio signals, and graphing signals for output to the display device, audio device, storage device, and/or charting device.

Figure 3:
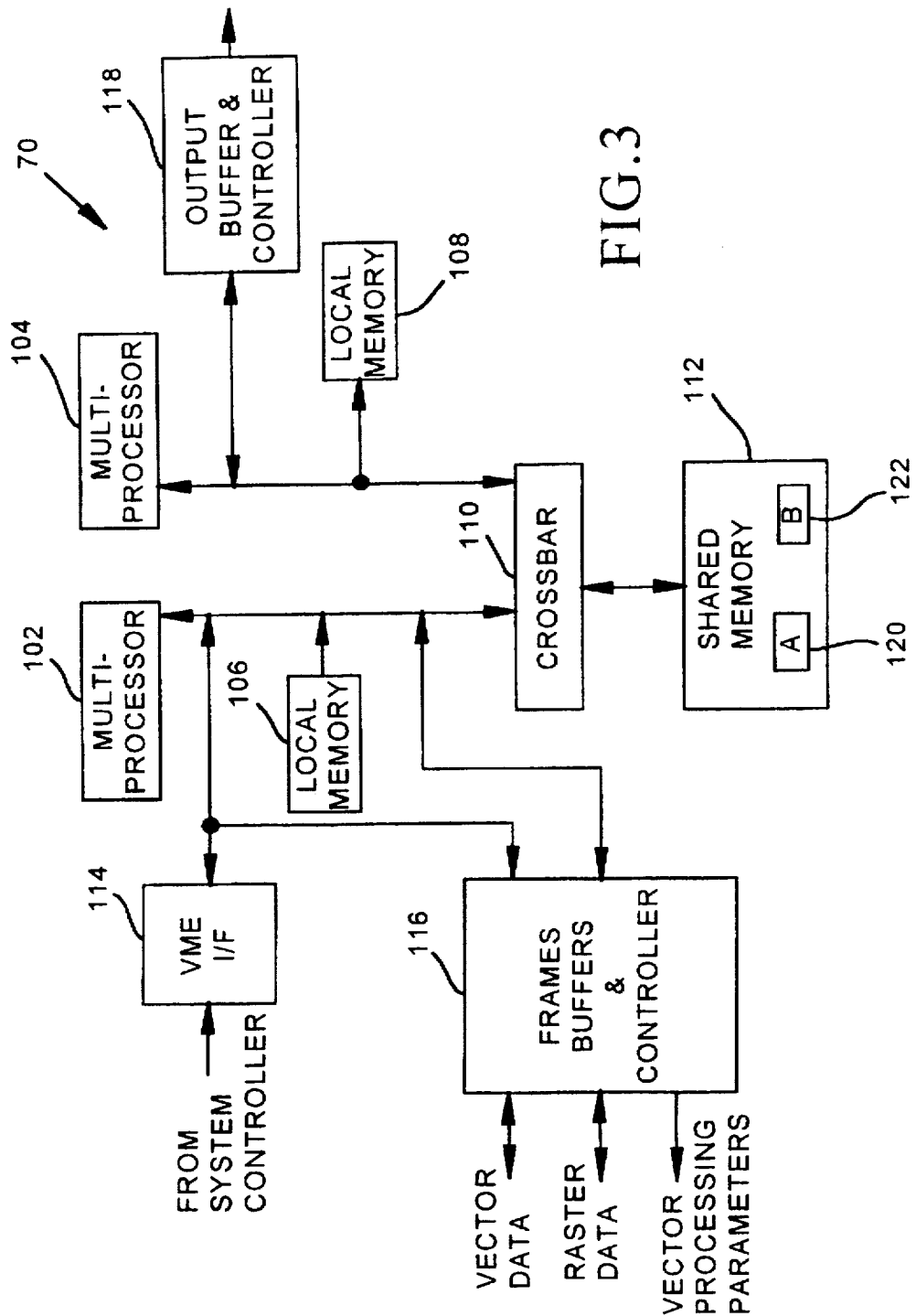
FIG. 3 is a block diagram of the programmable ultrasound signal processing apparatus for implementing the method of this invention.

FIG. 3 is a block diagram of a programmable processor subsystem 70 for implementing one or more of the tasks 32–40. In a preferred embodiment subsystem 70 embodies or is part of the back-end subsystem(s) 30. In another embodiment subsystem 70 is an external processing subsystem receiving data from a subsystem 30 or other part of the system 10. Apparatus 70 includes multiple processors for performing various vector processing, image processing, scan conversion and/or video processing tasks. In a specific embodiment a pair of processors 102, 104 are included. The apparatus 70 also includes local memory 106, 108, crossbar switch 110, shared memory 112, interface 114, frame buffer/controller 116 and output buffer/controller 118.

Figure 4:
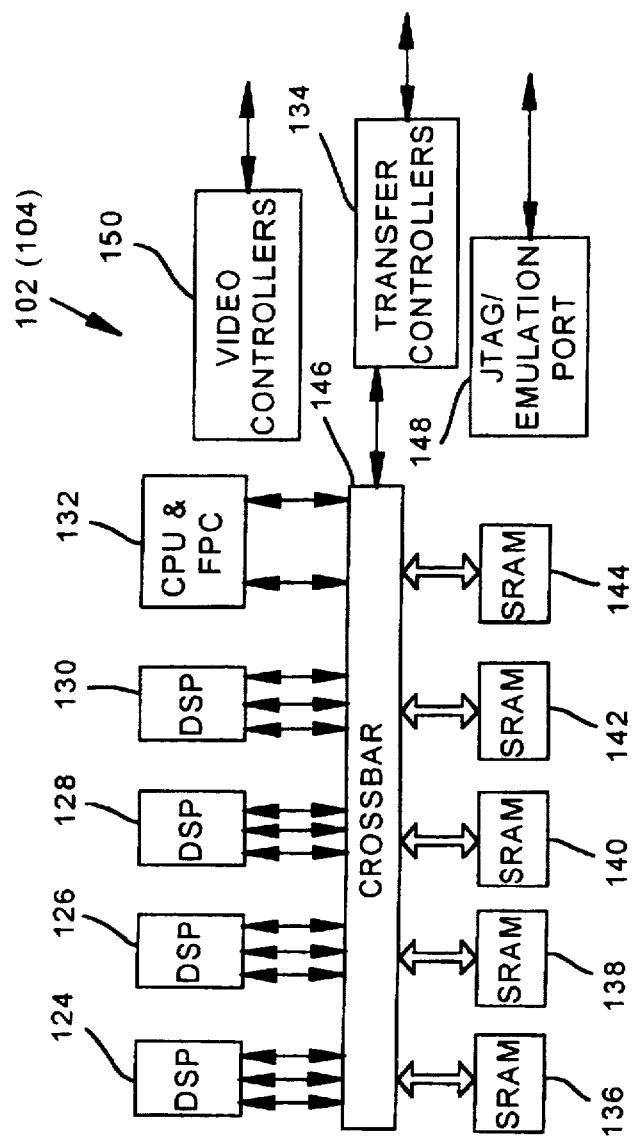
FIG. 4 is a block diagram for one embodiment of a multiprocessor of FIG. 3.

In one embodiment each processor 102, 104 includes one or more digital signal processors. In a specific embodiment each processor 102, 104 is a multiprocessor, such as a Texas Instruments multimedia video processor ("MVP") (part no. TMS320C80). FIG. 4 shows a block diagram of an MVP multiprocessor. The MVP combines on a single semiconductor chip, four fully programmable digital signal processors 124, 126, 128, 130 and a master processor 132 for handling multiple data streams via a transfer controller 134. Several on-chip random access memory (RAM) devices 136, 138, 140, 142, 144 serve as resident memory accessible to the digital signal processors (DSPs) 124–130 via a crossbar network 146. The MVP has a throughput rating of approximately 2 billion operations per second. The master processor 132 is a RISC processor with an integral floating point unit. According to this embodiment the master processor 132 coordinates and distributes processing tasks among the DSPs 124–130 and manages external off-chip communications. A JTAG/emulation port 148 is included for aid in testing, development and diagnostics.

Each DSP 124–130 includes two address generators, three input 32-bit ALUs, a 16×16 multiplier, three zero-overhead loop controllers, and a 32-bit barrel shifter. Each RAM 136–144 has a 10 kB capacity providing 50 kB of single-cycle SRAM. Memory 136–144 is partitioned in blocks with each block serving as either data RAM, parameter RAM, data cache or instruction cache. The transfer controller 134 services the on-chip caches and interfaces to external memory (e.g., local memory 106 or 108, and shared memory 112).

The MVP also includes a pair of video controllers 150. Controllers 150 generate video synchronization signals or synchronize data transfer rates with external video signals.

Referring again to FIG. 3, each multiprocessor 102, 104 has a respective dedicated local memory 106, 108, serving as a secondary cache. Each local memory 106, 108 has capacity for storing a frame of ultrasound data. In one embodiment a 2 MB capacity is provided at each local memory 106, 108. In addition shared memory 112 is included. In one embodiment shared memory 112 is implemented as two separate 64 MB memory banks 120, 122 for a total of 128 MB shared memory. The storage capacity of local memory 106, 108 and shared memory 112 varies for alternative embodiments. The multiprocessors 102, 104 access shared memory through crossbar switch 110. For a two multiprocessor embodiment, a 2×2 crossbar switch is implemented. The purpose of the crossbar switch 110 is to allow the multiple processors 102, 104 simultaneous access to the shared memory banks. The crossbar switch 110 includes a pair of transceivers for each input channel, along with a crossbar controller.

The function of the crossbar controller is (i) to manage requests for access and (ii) to refresh shared memory 112. If a multiprocessor 102 requests access to a shared memory bank 120, 122 not currently being accessed by the other multiprocessor 104, then the access is granted. If the multiprocessor 102 requests access to a shared memory bank 120, 122 currently being accessed, then the multiprocessor 102 waits until the memory bank is available. Simultaneous access to a shared memory bank 120, 122 thus is available when the accesses are to separate memory banks. For reconciling simultaneous requests for access, one multiprocessor 102 is prescribed to have priority for a specific one shared memory bank 120, while the other multiprocessor 104 is prescribed priority for the other shared memory bank 122. If both multiprocessors 102, 104 request access to a common bank, then the processor with the prescribed priority for that bank is granted access. However, to avoid lengthy delays, the other multiprocessor is granted access after the current access, even if the higher priority multiprocessor comes right back with a second request. For example, consider the case in which multiprocessor 102 has the prescribed priority to the first memory bank 120. The first multiprocessor 102 makes two sequential requests for access to bank 120, while multiprocessor 104 also makes a request to bank 120. Because of the prescribed priority, the first multiprocessor 102 is granted access for its first request. Next, however, the second multiprocessor 104 is granted access. Then, the first multiprocessor 102 is granted access for its second request.

System control signals are received by apparatus 70 from the system controller 14 via an interface 114. The frame buffer/controller 116 serves as a data interface with the ultrasound front end (e.g., beamformer 20), the back-end processing subsystem 30, or another subsystem 30. The output buffer/controller 118 serves as a data interface between the apparatus 70 and the back-end processing subsystem 30 or another subsystem 30, and/or one or more output devices.

Data Acquisition

To perform 3D image generation the relative position and orientation of respective image frames is obtained. Indicators of position and orientation for a given frame are obtained in one embodiment using a 3D magnetic position sensor 13. An exemplary sensor 13 is a Polhemus 3Space FasTrak sensor from Polhemus, Inc. of Colchester, Vt. The sensor 13 includes a receiver and a transmitter. The sensor's receiver is mounted to or integrated with an ultrasound scanning probe which houses the transducer 12. The sensor's transmitter is located within 1 meter of the sensor's 13 receiver. The sensor 13 generates six degree-of-freedom position measurements (three positions, three orientations). The Polhemus sensor is accurate to within ±0.8 mm for position and ±0.15° for orientation. For each image frame received for back-end processing, the position and orientation indicators are received from the sensor 13. The sensor 13 indicates the position and orientation of the sensor 13 receiver. The receiver is in a fixed position and orientation relative to the transducer 12. Thus, the indicators are adjusted to correspond to the position and orientation indicators for the transducer 12. By reading the sensor 13 receiver values when sampling the transducer 12 receiver the sensor indications are synchronized to those for the image frame being sampled.

Volume Reconstruction

Figure 5:
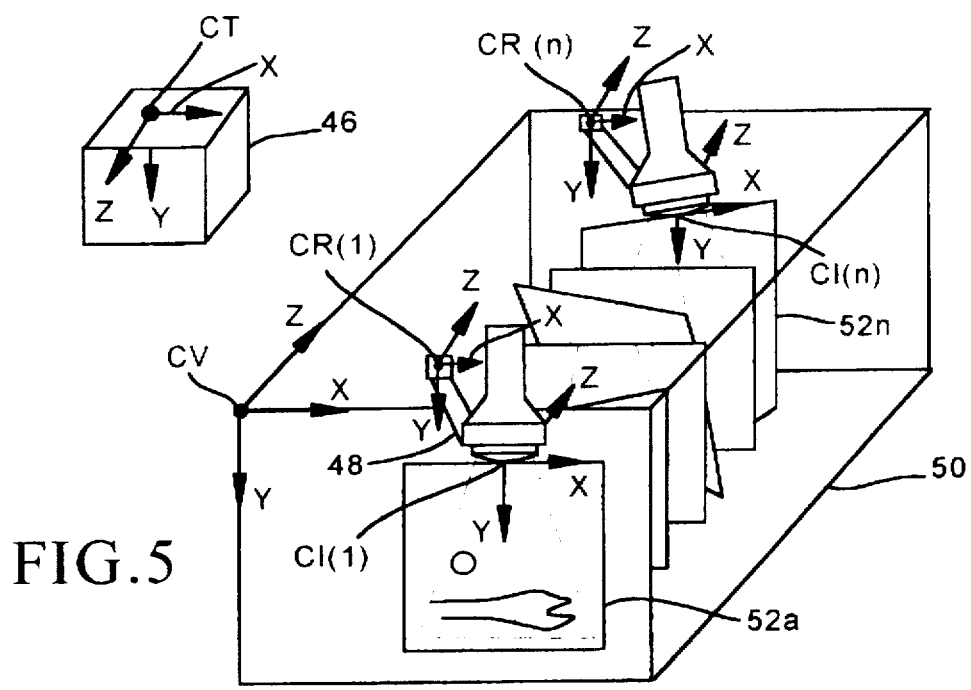
FIG. 5 is a diagram of registered image planes reconstructed within a reference volume according to one embodiment of this invention.

To reconstruct the image planes corresponding to a sequence of free-hand scans, the coordinates of each pixel for each given image plane are transformed into coordinates in a reference coordinate system. To perform the transformation, the relationships between the reference coordinate system and each image plane coordinate system is determined. FIG. 5 shows the various coordinate systems, including the image plane coordinate system (CI), the sensor 13 transmitter coordinate system (CT), the sensor 13 receiver coordinate system (CR), and the reference coordinate system (CV). The position and orientation indicators for a given image plane (as determined from the sensor 13 position and orientation indicators) recorded during volume acquisition determine the transformation for an image sample point coordinate $CI(x_n, y_n, z_n)$ into the reference coordinate system. Each pixel's brightness in the image plane is distributed over the surrounding voxels of the reconstruction volume using an interpolation scheme. In one embodiment sample data for a point in the image coordinate system is allocated among 8 nearest neighbor voxels within the reference coordinate system. To compensate for undersampling, in some embodiments the reconstruction process distributes pixel values beyond just the eight adjacent or surrounding voxels.

Coordinate System Transformations

To register each image plane in the reference coordinate system, the coordinates of each pixel in each acquired image plane are transformed into the reference coordinate system. The position sensor 13 tracks the position and orientation of each image plane by providing three position indications and three orientation indications (data for 6 degrees of freedom). Each time an image frame is gathered, position measurements from the position sensor 13 are acquired. The position measurements obtained from the position sensor 13 describe the position and orientation of the receiver's coordinate system (CR) with respect to the transmitter's coordinate system (CT) in 3D space. Six parameters completely describe the position and orientation of the receiver's coordinate system with respect to the transmitter's coordinate system: {tx, ty, tz, θx, θy, θz}, where tx, ty, and tz are the translations in the x, y, and z directions between the origin of the transmitter's coordinate system and the origin of the receiver's coordinate system, respectively; and θx, θy, θz are the rotations of the receiver's axes around the transmitter's x, y, and z axes, respectively.

During volume acquisition, prior to each image being digitized, the six element position measurements describing the relative position and orientation of the receiver 48 in relation to the transmitter 46 are derived. Because the receiver 48 does not precisely coincide with the ultrasound transducer 12, the position and orientation measurements do not directly describe the location and orientation of the acquired image. Specifically, the image plane coordinate system for a current image is offset from the sensor receiver coordinate system at the time such image is captured. Furthermore, when subsequent images and position/orientation measurements are acquired, the relative position and orientation of these new images need not be parallel to those of prior images. The operator is free to move the probe about a number of degrees of freedom. Although the number of degrees of freedom can be limited in some embodiments, in one embodiment there are six degrees of freedom (e.g., no limitation on the probe movement).

The reference coordinate system CV(x,y,z) is the coordinate system for the reconstruction volume 50(CV). The reconstruction volume is the bounding box that encompasses the acquired images 52a-52n. The first image 52a occurs within the reference coordinate system's xy plane where z=0. One corner of the reconstruction volume 50 serves as the origin CV(x=0,y=0,z=0) of the reference coordinate system. Such origin also corresponds to the starting address of the reference volume 50 in memory. In one embodiment the reconstruction volume is a rectilinear volume occurring in the first quadrant of the reference coordinate system (e.g., x is positive, y is positive and z is positive). For example, one boundary of the volume 50 occurs at the plane z=0, another boundary occurs at the plane x=0 and another boundary occurs at the plane y=0. Such planes are in the reference coordinate system. As a result, all pixel coordinates for sample points within the reference volume are positive in the reference coordinate system. One advantage of generating only positive coordinates in the reference coordinate system, CV, is that the coordinates are used to index the reconstruction volume as it is stored in memory, (e.g., image memory is mapped to the reference coordinate system and coordinates are used to index into the memory).

Before the coordinates of each pixel in the i-th image 52i are transformed into the reference coordinate system, the spatial coordinates of each image's pixels in that image's coordinate system CI(i) are obtained. The origin for any i-th image plane coordinate system CI(i) is defined as the top center of the image 52i, with the top row of the image serving as the $x_i$ axis, and the center column of the image serving and the $y_i$ axis. In computing the coordinates of each pixel in a CI(i) coordinate system, the z coordinate of each pixel in the image 52i is zero. Also, the $x_i$ and $y_i$ axes are parallel to the rows (r) and columns (c), respectively, of such image 52i. The $(x_i, y_i, z_i)$ coordinates of each pixel (c, r) in an image 52i are derived as follows:

$$x = \left( c - \frac{N_c}{2} \right) \frac{D_x}{N_c} \; ; \; y = \left( r - \frac{N_r}{2} \right) \frac{D_y}{N_r} \; ; \; z = 0 \qquad (1)$$

where $N_c$ is the number of image columns, $N_r$ is the number of image rows, $D_x$ is the physical width of the scanned region, and $D_y$ is the physical height of the scanned region (in millimeters). Because the number of image columns, the number of image rows, the physical width and the physical height are the same for each image plane 52$i$, the coordinates of each pixel in an i-th image 52$i$ in the image's coordinate system CI(i) need be computed only once. A coordinate for the first pixel in the first row of any image plane 52$i$ is the same for each image plane 52$a$ to 52$n$.

To transpose the image plane coordinate system CI(i) coordinates of each pixel in an i-th image plane 52$i$ with respect to the common reference coordinate system, the relationships between the various coordinate systems are derived. The relationships between the transmitter's 46 coordinate system CT, the receiver's 48 coordinate system CR, the image's coordinate system CI, and the reference coordinate system CV are represented in transformation matrices. The transformation matrices include the rotations and translations required to transform coordinates from one coordinate system to another coordinate system.

At a first step in the volume reconstruction process, a first image plane 52$a$ is received based upon echo signals received at the transducer 12. In addition, position and orientation indicators are received from the sensor 13 receiver 48. The coordinates of each sample point in the image plane 52$a$ then are defined based upon equation (1) above. A z-axis of the reference coordinate system CV is defined to be in the direction of a normal vector of the image plane 52$a$. The origin of the z-axis of the reference coordinate system is on the image plane 52$a$. The directions of the x-axis and y-axis of the reference coordinate system are taken to be the direction of the image plane 52$a$ coordinate system x-axis and y-axis. The origin of the reference coordinate system x-axis and y-axis are prescribed as offsets from the image plane 52$a$ coordinate system CI($a$) x-axis and y-axis. Thus, the image plane 52$a$ occurs within plane z=0 of the reference coordinate system and is offset from the origin of the reference coordinate system. The origin of the reference coordinate system is selected to position the image plane 52$a$ within the first quadrant of the reference coordinate system (see FIG. 5). Preferably the origin is offset enough from the image plane coordinate system CI($a$) origin such that each subsequent image plane is likely to occur within the first quadrant of the reference coordinate system. However, in some embodiments there is no assurance that every pixel of each subsequent image frame 52$b$–52$n$ will occur within the first quadrant of CV. For example, for a free-hand scan the operator is free to move the ultrasound transducer 12 in any of 6 degrees of freedom to scan a desired target area of a patient. According to one embodiment, any portion of subsequent image planes 52$b$–52$n$ which does not occur within the first quadrant of the reference coordinate system is ignored. Specifically such portions do not occur within the reference volume 50 being constructed.

With the origin and axes of the reference coordinate system defined, the task is to register subsequent image frames in the reference coordinate system CV. To do so, the coordinate system for a given subsequent image plane is defined and transformed into the reference coordinate system. Specifically, the coordinates of each sample point of any image plane i=K (where K>1) are transformed into the reference coordinate system CV by a series of transformations. The series of transformations includes: (i) transforming from the image plane coordinate system CI(K) to the receiver coordinate system CR(K); (ii) transforming from the receiver coordinate system CR(K) to the transmitter coordinate system CT; and (iii) transforming from the transmitter coordinate system to the reference coordinate system.

In applications where the transmitter 46 is fixed during the scans, the transformation process is simplified in that the transformation from the transmitter coordinate system CT to the reference coordinate system CV is the same for each image plane K.

For a given image plane i=K (K>1), the image plane coordinates are transformed into the receivers coordinate system CR(K) using a transformation matrix P. The transformation matrix P, which describes the relationship between the image's coordinate system and the receiver's coordinate system is fixed for each image plane. This is because the sensor receiver 48 is fixed relative to the ultrasound transducer 12. Thus, matrix P is the same for each image plane 52 acquired. The inverse matrix of matrix P is matrix $P^{-1}$. The intermediate coordinates are transformed into the transmitters coordinate system CT using a transformation matrix $A_K$. The transformation matrix $A_K$ describes the relationship between the receiver's coordinate system CR at the time image K is obtained and the transmitter's coordinate system CT at such time. When the operator moves the transducer 12 the transformation matrix $A_K$ differs for each acquired image plane 52. The transformation matrix $A_K$ is formed from the corresponding 6 degree of freedom position and orientation measurements, {tx, ty, tz, θx, θy, θz}, acquired from the position sensor 13. The intermediary coordinates in the transmitter's coordinate system CT then are transformed into the reference coordinate system CV using a transformation matrix $T_A$. For applications where the transmitter is stationary during scanning, the transformation matrix $T_A$ is the same for each image plane. After the series of transformations the results are coordinates for the image data within the reference coordinate system.

The transformation process for subsequent image frames after the first image frame 52$a$, in effect is one of transforming the coordinates into the coordinate system of the first image plane 52$a$. This is because the x and y axes of the first image plane are parallel to those of the reference coordinate system and because the z axis coincides. The statement is not precisely correct, though, because the reference coordinate system origin is offset from the first image plane coordinate system along respective x and y axes.

The equation for transforming an image plane into the reference coordinate system is given below as equation (II):

$$I_v = (T_A P^{-1} A_1^{-1} A_K P) I_K \text{ or } I_v = T_K I_K \qquad (II)$$

where $I_K$ is a vector containing the coordinates of a pixel in the image plane coordinate system CI(K);

$I_V$ is a vector containing the coordinates of the same pixel transformed into the reference coordinate system CV;

$A^{-1}_1$ is an inverse matrix transforming from the receiver coordinate system for image plane 1, CR(1), into the transmitter coordinate system CT; and $T_K$ is the complete transformation matrix representing the transformation from image plane K's coordinate system CI(K) to the reference coordinate system, CV.

A transformation matrix is a 4×4 matrix used to transform coordinates (represented as a vector) from one coordinate system to another coordinate system. Transformation matrices are formed from the six parameters {tx, ty, tz, θx, θy, θz}. The transformation matrix, $T_K$ is given by:

$$T_K = \begin{bmatrix} |R_{3\times3}| & |T_{3\times1}| \\ |O_{1\times3}| & 1 \end{bmatrix},$$

where $R_{3\times 3}$ (R=rotation) is given by the product:

$$R_{3\times 3} = \begin{bmatrix} \cos\theta_z & -\sin\theta_z & 0 \\ \sin\theta_z & \cos\theta_z & 0 \\ 0 & 0 & 1 \end{bmatrix} \begin{bmatrix} \cos\theta_y & 0 & \sin\theta_y \\ 0 & 1 & 9 \\ -\sin\theta_y & 0 & \cos\theta_y \end{bmatrix} \begin{bmatrix} 1 & 0 & 0 \\ 0 & \cos\theta_x & -\sin\theta_x \\ 0 & \sin\theta_x & \cos\theta_x \end{bmatrix}$$

$T_{3\times 1}$ (T=translation) is given by:

$$T_{3\times 1} = \begin{bmatrix} t_x \\ t_y \\ t_z \end{bmatrix}$$

$O_{1\times 3}$ is a 1×3 row vector composed of zeroes, and $t_x$, $t_y$, $t_z$, $\theta_x$, $\theta_y$, and $\theta_z$ are defined as above. The coordinates are represented as a vector, such as $I_K$ and $I_V$.

$$I_K = \begin{bmatrix} x_K \\ y_K \\ z_K \\ 1 \end{bmatrix} ; I_V = \begin{bmatrix} x_V \\ y_V \\ z_V \\ 1 \end{bmatrix}$$

Interpolation

In addition to transforming the coordinates into the reference coordinate system, another step is to perform interpolation so that the transformed points occurs at discrete coordinates, (i.e., occur on a discrete cartesian grid of the reference coordinate system). Specifically, some image plane sample points may occur between discrete coordinate points (e.g., have a non-integer x-coordinate, y-coordinate and/or z-component).

According to varying embodiments a single nearest neighbor or a distribution among nearest neighbors is used to perform the interpolation. For a single nearest neighbor scheme, the reference coordinate system coordinate is computed as follows (C programming language terminology):

```
xlow = floor (x1);
ylow = floor (y1);
zlow = floor (z1);
for (zinc = 0; zinc <= 1; zinc++)
    for (yinc = 0; yinc <= 1; yinc++)
        for (xinc = 0; xinc <= 1; xinc++){
            addr = xlow+xinc + (ylow+yinc)*vol_width +
                    (zlow+zinc)*vol_width*vol_height;
            recon_vol[addr] = pixval
}
``` where x1, y1, and z1 are real-valued coordinates of a current pixel in the reference coordinate system; vol_width is the width of the reconstruction volume; vol_height is the height of the reconstruction volume; and recon_vol is the reconstruction volume.

For a first order interpolation in which a real-valued coordinate in the reference coordinate system is distributed among eight surrounding nearest neighbors (voxels), an accumulator array and a weight array are used. The accumulator array determines the contribution of each real-valued coordinate input pixel onto each discrete-valued coordinate output pixel. A weight $w_i$ is related to the distance between a given input pixel and output pixel. The accumulator array contains the sum:

$$O_{xyz} = \sum_{i=1}^{N} w_i * I_i \quad \text{(III)}$$

where $w_i$ is weight related to the distance of each real-valued coordinate input pixel to the surrounding discrete-valued coordinate output pixels; $I_i$ is the real-valued coordinate input pixel value; and N is the number of contributions for output location $O_{xyz}$. The weight array integrates the weights applied at each output location and normalizes the output values. In a preferred embodiment the first order interpolation is used to distribute the real-valued coordinate value among several nearest neighbor discrete-values coordinates. In one embodiment the value is distributed among 8 nearest neighbors (e.g., which form a cube around the real-valued coordinate). To minimize the number of gaps that would occur in a reconstructed volume after distributing the real-valued coordinate value, distribution is allocated among a larger number of voxels in an alternative embodiment.

The sample data values or the interpolated values derived from the sample data are stored in memory. The address space for such memory is mapped to the reference coordinate system. Thus, values for a given row of a given reference volume slice 52i (taken along for example the z-axis of the reference coordinate system) are stored in sequential address locations. Also, values for adjacent rows in such slice 52i are stored in adjacent first memory address space.

Implementation on Multiprocessor

To implement the reconstruction algorithm on a multiprocessor 102/104, the coordinate computations and the pixel interpolation tasks are divided equally among the 4 DSPs 124–130. The input data for the nearest neighbor distribution reconstruction are processed as independent tasks so synchronization among the DSPs is not required. Because the CPU 132 has a floating point unit, it is used to perform all of the transformation matrix computations and generations required to transform the pixel coordinates of a given image into the reference coordinate system.

The CPU 132 also coordinates the processing tasks among the DSP 124–130. For each image K acquired, the CPU 132 reads the corresponding position and orientation measurements recorded from sensor 13 and computes the transformation matrices $A_K$ and $T_K$. To reduce the number of operations performed per pixel and to transform the computations into a form more compatible with th DSPs 124–130, equation (II) above is simplified. Computing the coordinates of a given pixel in the reference coordinate system is performed by adding an offset to an adjacent pixel's previously computed coordinates. Thus, rather than performing 16 multiplications and 12 additions per pixel, the coordinates are derived by just 3 additions. A total of six offsets are computed. There are three offsets for computing the x, y, and z coordinates in the x-direction (along the row of the image), and three offsets for computing the x, y, and z coordinates in the y-direction (down the column of the image). The offsets are found in the computed $T_K$ transformation matrix and:

$$\Delta x_x = T_K[0, 0] \qquad \Delta y_x = T_K[0, 1]$$
$$\Delta x_y = T_K[1, 0] \qquad \Delta y_y = T_K[1, 1]$$
$$\Delta x_z = T_K[2, 0] \qquad \Delta y_z = T_K[2, 1]$$

where $\Delta x_x$, $\Delta x_y$, $\Delta x_z$ are the x, y, and z offsets in the x-direction, and $\Delta y_x$, $\Delta y_y$, $\Delta y_z$ are the x, y, and z offsets in the y-direction.

Each DSP 124–130 is assigned a quarter of the image plane to distribute into the reconstruction volume. For each DSP, the CPU 132 initiates the processing and passes the starting pixel coordinate for their section of the image plane, as well as the six offsets. Because the DSPs 124–130 do not have a floating point unit, the starting coordinate and the six offsets are converted to fixed point, Q12 format. Each of the DSPs 124–130 processes a portion of the image plane's pixels, and calculates the reference system coordinates for each of the pixels. To compute the new coordinates along a row:

$$x=x+\Delta x_x, y=y+\Delta x_y, z=z+\Delta x_z$$

and to compute the new coordinates along a column:

$$x=x+\Delta y_x, y=y+\Delta y_y, z=z+\Delta y_z$$

Once the coordinates for a given pixel are computed, the offset in the reconstruction volume is computed. One offset is computed—the offset of the neighbor with the smallest x, y and z coordinate. The resulting 32-bit offset is stored on-chip and used to generate a table used by the transfer controller 134.

The transfer controller 134 transfers data from on-chip to off-chip memory using a starting address and memory offsets stored in a memory location. In one embodiment the transfer controller 134 is programmed to transfer the three-dimensional, 8-pixel cube to the start address of the reconstruction volume, plus the offset computed by the DSP and stored in one of the DSPs memory modules (136–142).

Incremental Reconstruction

To perform the incremental reconstruction, the CPU 132 computes both the $T_K$ matrix and its inverse $T_K^{-1}$. Then, the corners of the reconstruction volume are computed and compared with the coordinates of the bounding volume 50. The intersecting portion of the acquired image are determined and the bounding coordinates are converted back to the image's coordinate system. The start coordinates of a sub-image are determined and the sub-image is divided equally among the 4 DSPs 124–130 for distribution into the reconstruction volume 50.

An additional step is the computation of an orthogonal projection of the current state of the reconstruction volume, so that the volume can be seen to grow during the scan. An orthogonal projection is used because its computation is simpler to render (no interpolations need to be computed to transform from the reference coordinate system to a displayed image raster coordinate system). A maximum intensity projection (MIP) rendering scheme is used in which a ray is cast along the depth of the volume, and the maximum value encountered is the value that is projected for that ray (e.g., the value used to derive a pixel for a given raster point on the 2D image projection). This rendering algorithm is computed efficiently on the multiprocessor 102/104. The volume to be rendered is equally divided among the 4 DSPs 124–130. Each DSP loads two rows, and compares the corresponding pixels on the two rows and keeps the larger of the two pixels. Since 8 bit/pixel data is used and the 32-bit arithmetic unit can be allocated as four 8-bit units, each DSP computes the maximum of 8 pixels in two cycles. The DSPs then output the rows to a display unit or to an intermediary video processing process where pixel data is derived from the image data (i.e., the sample point values or the interpolated values derived from the sample points) stored in the reference volume address space.

Image Reconstruction Results

Each DSP 124–130 begins by replicating the input pixels 8 times and storing them in on-chip RAM (136–142). For each pixel, this occurs as one load operation, replication of the 8-bit pixel value 4 times into a 32-bit word (the MVP has an arithmetic command to perform this operation in one cycle), and two stores. Using the instruction-level parallelism capability of the MVP, all operations are performed in two cycles per pixel. After the pixels are replicated, the DSPs 124–130 compute the 32-bit offsets needed to distribute (interpolate) to the 2×2×2 regions. To compute the new x, y, z coordinates using the D offsets requires 3 additions. To compute the 32-bit offset from the x, y, z coordinates requires two multiplications, three logical 12-bit shifts (to convert from fixed point Q12 format), to additions, and one store (to store the 32-bit offset in the guide table). Again, using the instruction-level parallelism capability of the MVP, such operations are completed in 8 cycles per offset.

For 512×512 ultrasound image frames, volumes were reconstructed using an forward-mapper zero-order interpolation scheme at 64 ms/frame (15.6 frames/sec). The main tight loop of the DSPs 124–130 which replicates each pixel to the eight neighbors and calculates the 32-bit offset for insertion into the reconstruction volume requires 10 clock cycles/pixel. With 4 DSPs 124–130 running concurrently, such time is reduced to 2.5 clock cycles/pixel. For 512×512 input images and an MVP 102 running at 50 MHz, the coordinate computation and offset calculation complete in approximately 13.1 ms. However, since the computation and I/O operations are performed concurrently on separate MVPs 102, 104, the table-guide I/O operations dominate the reconstruction process requiring 64 ms/ frame.

For sequences of 512×512 ultrasound image frames, and a 128×128×128 reconstruction volume, volumes were reconstructed using the incremental volume reconstruction scheme at 80.3 ms/frame (12.5 frames/sec). The rendering algorithm is optimized to process 8 voxels each cycle using all 4 DSPs 124–130. Using a 50 MHz MVP 102 and computing the orthogonal projection of a 128×128×128 volume, the orthogonal projection is determined in 260,096 cycles (5.2 ms). Because only 8 voxels are brought on chip every two cycles, the process is I/O bound resulting in an orthogonal projection for a 128×128×128 volume in 10.5 ms. Overhead for the transfer controller packet request setup, plus transfer controller operations for performing video and DRAM refresh increase the time to 16.3 ms to perform the image processing for a 128×128×128 volume. Thus, a target volume is incrementally reconstructed and displayed in real time on an ultrasound medical diagnostic imaging system. One advantage of incrementally constructing the target volume in real time is that the operator can see the target volume as it is being scanned. If the scan is too fast for example causing pockets of blank screen within the reference volume where data samples were not achieved, then the operator can go back over the empty areas by moving the transducer probe back over the corresponding area of the patient's anatomy. Thus, the operator can view the target volume and scan effectiveness in real time and improve the displayed images by deliberately scanning desired areas repeatedly or at a slower speed. By slower speed, it is meant that the operator moves the transducer probe over the patient more slowly.

According to another embodiment or operator selection, the 3D volume is fully reconstructed before being displayed. Thus, the volume is not incrementally displayed in such alternative mode or embodiment.

Image Visualization

After the 3D volume is constructed and displayed, the operator is able to alter the viewing angle of the image. For example the operator can view the volume from any angle or position and can also specify a subvolume to render. These operations occur in real time. In addition, the operator can stop the incremental volume construction in process and work with the volume portion displayed to rotate the volume portion or change the viewing angle of such volume portion. The operator also can recommence volume construction at the new viewing angle.

The image visualization process derives 2D image projections of the 3D volume over time to generate a rotating image or an image at a new viewing angle. A shear warp factorization process is used to derive the new 2D projection for a given one or more video frames of the image. For each change in viewing angle, the process factorizes the necessary viewing transformation matrix into a 3D shear which is parallel to slices of the volume data. A projection of the shear forms a 2D intermediate image. A 2D warp is implemented to produce the final image, (i.e., a 2D projection of the 3D volume at a desired viewing angle). A sequence of final images at differing viewing angles is used to create a real-time rotating view of the target volume.

Figure 6:
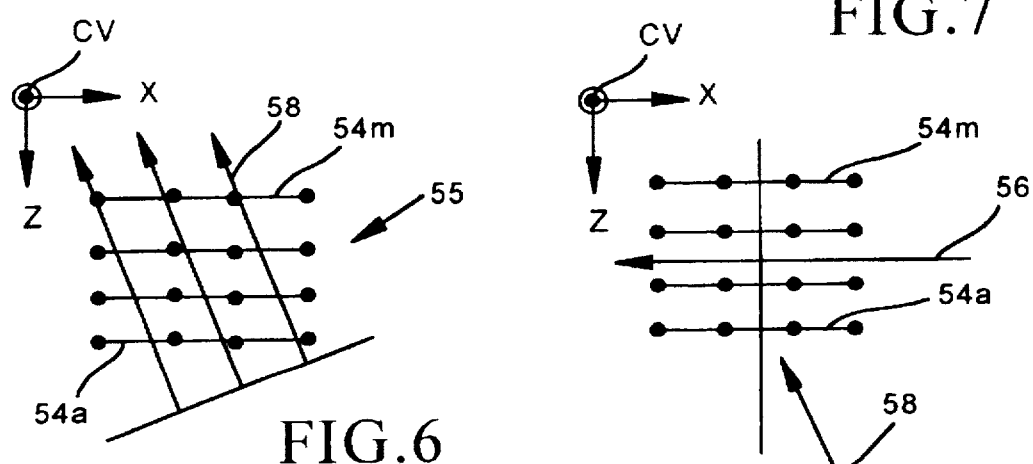
FIG. 6 is a diagram of reference volume slices and a desired viewing angle of the volume.
Figure 7:
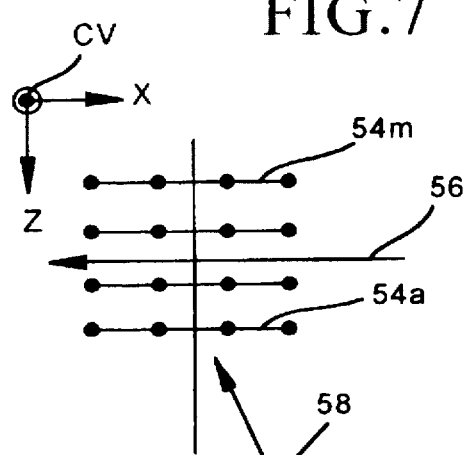
FIG. 7 is a diagram of the slices of FIG. 6 showing the shear direction.
Figure 8:
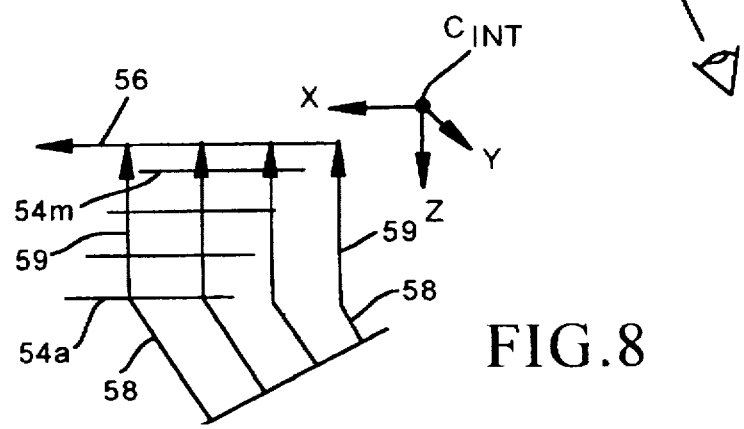
FIG. 8 is a diagram of the slices of FIG. 6 showing the shear direction and warped viewing plane direction.

During the process of revisualizing the volume at a different viewing angle, the reconstructed volume is sheared by transforming the reference coordinate system to an intermediate coordinate system. This simplifies mapping of the data. The intermediate coordinate system also is referred to as "sheared object space". The sheared object space is selected so that all viewing rays are parallel to one of the axes of the original coordinate system for the volume (e.g., the reference coordinate system). FIG. 6–8 depict the transformation into sheared object space. The volume 50 is stored in memory mapped to the rows and columns of the reference coordinate system CV. The volume is retrieved as a set 55 of volume slices 54a to 54m. The shearing direction 56 (see FIG. 7) for the volume is parallel to the set 55 of slices. Alternatively, the set of slices are resampled to be parallel to the shearing direction.

The slices 54 then are translated and resampled as shown in FIG. 8 to achieve image projection rays 59 which are perpendicular to the slices 54. The intermediate image projection plane is parallel to the slices of the volume. Since all the projection rays 59 are perpendicular to both the projection plane and the slices 54, an imaging process for the projection causes the image data to be accessed in storage order. Because the shearing occurs only on two axes, a simple translation operation is used which does not require a lot of computations. The intermediate coordinate system thus is created by a simple bilinear interpolation. The result of the shear factorization is a distorted image projection. Such distorted projection is not displayed. Before the rotated volume is displayed, the projection undergoes a 2D geometric image warping operation to create a final 2D image projection of the rotated volume.

Shear Warp Factorization

A 3D rotation is represented as a 4×4 matrix $M_{rotation\text{-}3D}$. Such rotation can be represented in several alternate schemes. According to one embodiment the matrix is represented by roll angle ($\alpha$), pitch angle ($\beta$) and yaw angle ($\gamma$). Each motion is performed about fixed axes. The notation for the matrix is as follows:

$$M_{rotation\text{-}3D} = \begin{bmatrix} C\alpha & -S\alpha & 0 & 0 \\ S\alpha & C\alpha & 0 & 0 \\ 0 & 0 & 1 & 0 \\ 0 & 0 & 0 & 1 \end{bmatrix} \times \begin{bmatrix} C\beta & 0 & S\beta & 0 \\ 0 & 1 & 0 & 0 \\ -S\beta & 0 & C\beta & 0 \\ 0 & 0 & 0 & 1 \end{bmatrix} \times$$

-continued
$$\begin{bmatrix} 1 & 0 & 0 & 0 \\ 0 & C\gamma & -S\gamma & 0 \\ 0 & S\gamma & C\gamma & 0 \\ 0 & 0 & 0 & 1 \end{bmatrix}$$

where C represents cosine and S represents sine of the specified angle $\alpha$, $\beta$, or $\gamma$. This matrix becomes:

$$M_{rotation\text{-}3D} = \begin{bmatrix} C\alpha C\beta & (C\alpha S\beta S\gamma - S\alpha C\gamma) & (C\alpha S\beta C\gamma + S\alpha S\gamma) & 0 \\ S\alpha C\gamma & (S\alpha S\beta S\gamma + C\alpha C\gamma) & (S\alpha S\beta C\gamma - C\alpha S\gamma) & 0 \\ -S\beta & C\beta S\gamma & C\beta C\gamma & 0 \\ 0 & 0 & 0 & 1 \end{bmatrix} =$$

$$\begin{bmatrix} m11 & m12 & m13 & m14 \\ m21 & m22 & m23 & m24 \\ m31 & m32 & m33 & m34 \\ m41 & m42 & m43 & m44 \end{bmatrix}$$

The shear-warp method transforms this matrix via a shear and a warp transformation:

$$M_{rotation\text{-}3D} = M_{warp\text{-}3D} \cdot M_{shear\text{-}3D}$$

$M_{shear\text{-}3D}$ is the operation which transforms the object space to the sheared object space. The goal of this transformation is to shear the object coordinates until the new viewing direction 59 becomes perpendicular to the slices 54 of the volume 50 (See FIG. 8). In one embodiment the +Z axis is the direction in which 2D image slices are stored in memory. As shown in FIG. 8, the new viewing axis 59 is along the Z axis in order to access the memory in the order of storage (i.e., more efficient memory accesses). In the case where the viewing direction is different from the Z axis, another transformation prior to the shear is applied to rearrange the volume into a space where the principal viewing axis 58 is the closest to be parallel to the Z axis. This rearrangement (P) includes rotating the volume by 90 degrees. The price to pay for this rearrangement is considered minimal compared to the gain of being able to access the memory in the storage order. The rearrangement matrix, P, is one of three alternative matrices shown below depending on the case:

$$P = \begin{bmatrix} 1 & 0 & 0 & 0 \\ 0 & 1 & 0 & 0 \\ 0 & 0 & 1 & 0 \\ 0 & 0 & 0 & 1 \end{bmatrix}, \text{or} \begin{bmatrix} 0 & 1 & 0 & 0 \\ 0 & 0 & 1 & 0 \\ 1 & 0 & 0 & 0 \\ 0 & 0 & 0 & 1 \end{bmatrix}, \text{or} \begin{bmatrix} 0 & 0 & 1 & 0 \\ 1 & 0 & 0 & 0 \\ 0 & 1 & 0 & 0 \\ 0 & 0 & 0 & 1 \end{bmatrix}$$

The shear-3D matrix below shows the shear and translation coefficients.

$$M_{shear\text{-}3D} = \begin{bmatrix} 1 & 0 & S_i & T_i \\ 0 & 1 & S_j & T_j \\ 0 & 0 & 1 & 0 \\ 0 & 0 & 0 & 1 \end{bmatrix}$$

where $S_i$ is a shear coefficient along direction i and $S_j$ is a shear coefficient along direction j, and where there is no shearing along a third axis k.

The shear in one particular direction can be, depending on the viewing angle, either positive or negative. Thus, it can create backward addressing. For speed and efficiency it is desirable to have the projection image always be in the same "bounding box volume 50". It is preferable to avoid backward addressing. When appropriate, a translation is performed along one or two axes. When the shearing coefficient (an offset by which the slices are moved), is positive ($S \geq 0$), the slices move in the positive direction and the translation coefficient is set to zero (T=0). If the viewing angle creates a negative shearing (S<0), to compensate for the backward addressing, the translation is equal to the maximum absolute value of the negative offset (i.e., T=−S×(the number of slices perpendicular to the principal axis)).

The warp 3D matrix is also a 4×4 matrix. Because the intermediate projection is a 2D image projection, the matrix converts to a 3×3 matrix.

$$M_{warp-3D} = \begin{bmatrix} w11 & w12 & w13 & w14 \\ w21 & w22 & w23 & w24 \\ w31 & w32 & w33 & w34 \\ w41 & w42 & w43 & w44 \end{bmatrix} \Rightarrow$$

$$M_{warp-2D} = \begin{bmatrix} w11 & w12 & w14 \\ w21 & w22 & w24 \\ w41 & w42 & w44 \end{bmatrix}$$

Since the volume can be sheared along the two axes, there are four different cases as shown in FIGS. 9–12 where (i,j) represents the original sheared coordinate system and (u,v) the translated one. The small squares represent the slices of the original volume and their locations relative to the projected image (bigger square). Once the shear operation is performed, the rendering chosen can be applied on the volume with an efficient memory access pattern. After the shear and rendering, the intermediate result is a 2D image. This result represents a distorted image since the projection has been done in the sheared space. In order to get the final image, the intermediate result is transformed from the sheared space to the original orthogonal coordinate. The full shear-warp equation with the volume rearrangement (P) can be rewritten with $M_{transform}$ representing the viewing transform as follows:

$$M_{transform} = M_{warp-2D} \times M_{shear-3D} \times P$$

Multiplying $M_{shear-3D}$ and $M_{warp-2D}$ and comparing to the rotation matrix $M_{rotation-3D}$ yields the following transformation matrix. $M_{transform}$:

$$M_{transform} = M_{warp-2D} \cdot M_{shear-3D} =$$

$$\begin{bmatrix} w11 & w12 & (w11S_i + w12S_j + w13) & (w11T_i + w12T_j + w14) \\ w21 & w22 & (w21S_i + w22S_j + w23) & (w21T_i + w22T_j + w24) \\ w31 & w32 & (w31S_i + w32S_j + w33) & (w31T_i + w32T_j + w34) \\ w41 & w42 & (w41S_i + w42S_j + w43) & (w41T_i + w42T_j + w44) \end{bmatrix}$$

where w11=m11; w12=m12; w21=m21; w22=m22; w31=m31; w32=m32; w41=m41; w42=m42; and
where w13=m14−m11$T_i$−m12$T_j$ $w23 = m21T_i - m22T_j$ $w33 = 0$ $S_i = |m22m13 - m12m23|/|m11m22 - m21m12|$; and $S_j = |m11m23 - m21m13|/|m11m22 - m21m12|$.

Figure 9:
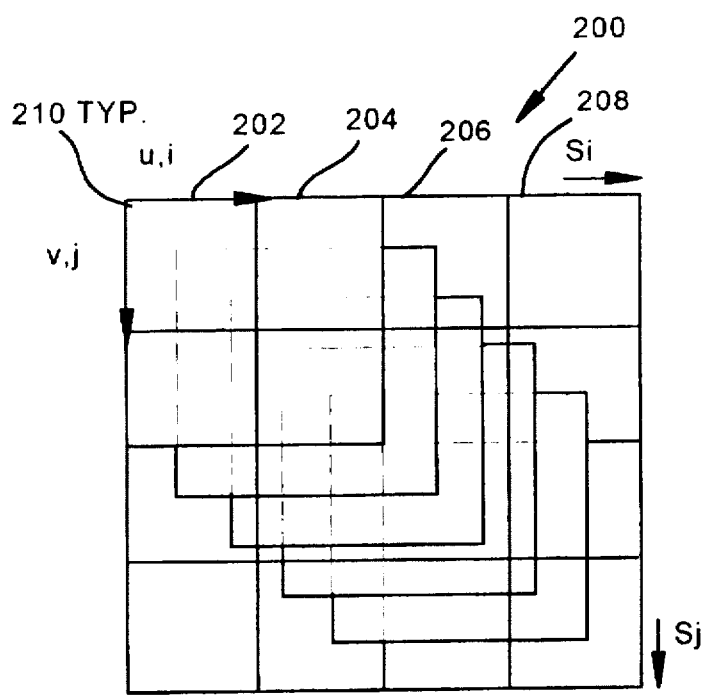
FIG. 9 is a diagram of one case of reference volume slices translated to an intermediate coordinate system.
Figure 10:
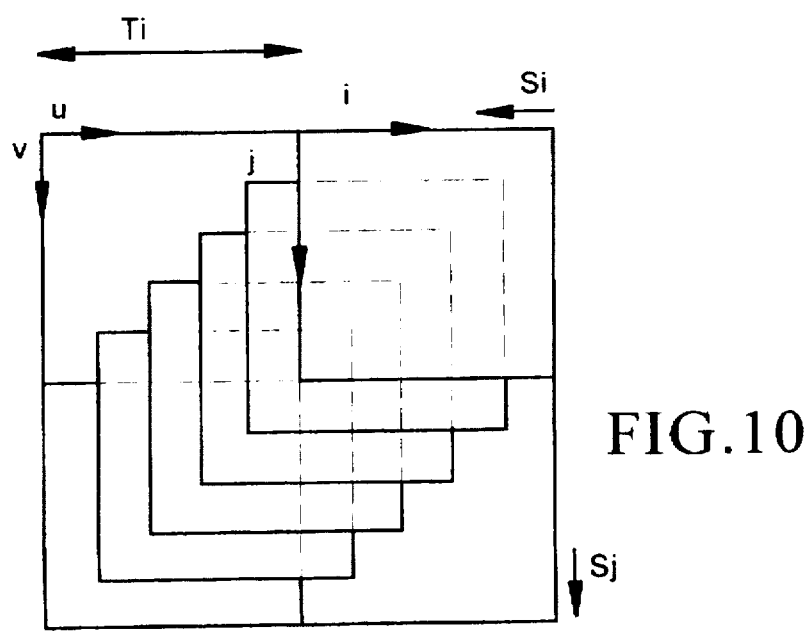
FIG. 10 is a diagram of a second case of reference volume slices translated to an intermediate coordinate system.
Figure 11:
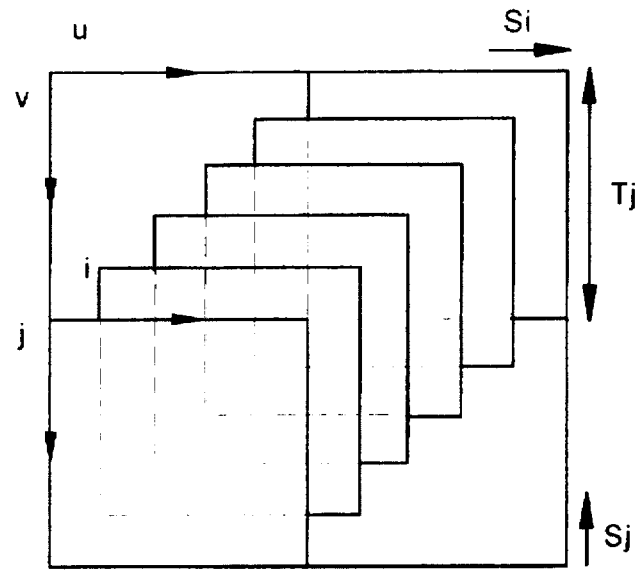
FIG. 11 is a diagram of a third case of reference volume slices translated to an intermediate coordinate system.
Figure 12:
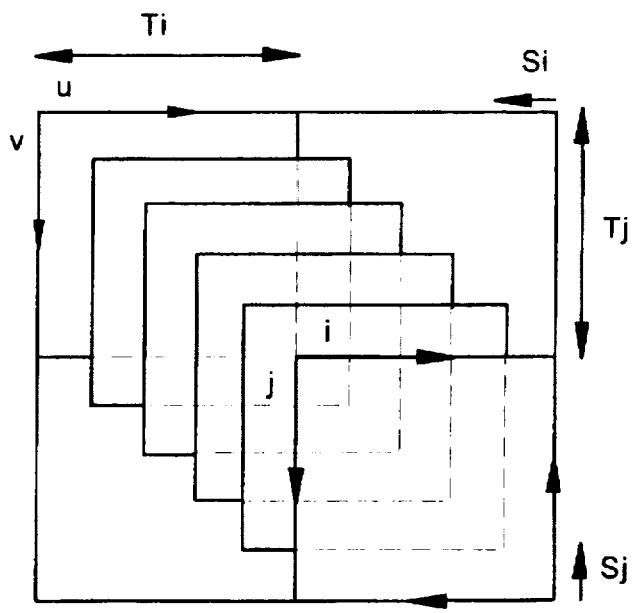
FIG. 12 is a diagram of a fourth case of reference volume slices translated to an intermediate coordinate system.

Distribution of the transformation among multiple processors is performed by calculating the size of the 2D output and dividing the area into sub-blocks fitting into a DSP 124–130's on-chip memory 136–142. The division is done first vertically then horizontally. After the division any intersection between the sub-blocks and the slices 54 are checked for. Once an intersection with a slice is determined the width and height of the common surface is derived. This common surface is one that is imported on-chip for processing that particular block and slice. FIG. 9 shows an example in which an image projection 200 is divided vertically among four sections 202, 204, 206, 208 corresponding to the four DSP 124–130. Each DSP is allocated data for one of the vertical sections. Within each vertical section are horizontal divisions or blocks 210. Data for the first block in each vertical division is moved on-chip by the transfer controller. While the appropriate DSP processes the first block in its vertical section, the transfer controller moves the second block on-chip for each DSP. While the DSPs 124–130 process the second blocks, the computation result for the first blocks are output and the data for the third blocks are loaded on-chip. The process continues in pipeline fashion to process all blocks of the projection. The processing performed on a given block identifies overlapping voxels on the projection 200 and determines for each set of overlapping voxels, which voxel is to be displayed. In one embodiment an MIP technique (maximum intensity projection), is used to select which voxel to display. Using an MVP it was found that the I/O operations occurred faster than the DSP computation operations. Thus, the I/O is transparent with the time to process the projection 200 determined by the computation time.

To avoid any gap in the division of the volume between the DSPs 124–130, each block has one column and one row in common with the two adjacent blocks. The size of the projected image is calculated in the shear space. From this "bounding box volume 50," the volume is divided in blocks small enough to fit in the on-chip memory. Each time a slice of the sheared volume intersects with a block located on-chip, the portion of the slice that is common with the block also is brought on-chip. As for the resampling, a bilinear interpolation is used where the interpolation coefficients are precalculated and stored in a LUT. Since the DSPs 124–130 only have fixed-point arithmetic capability, a Q7 format is used in representing real numbers for the interpolation and other calculations (e.g., position of a slice of the sheared volume relative to the frame).

The shear-warp implementation works in three steps. During a first step, each DSP 124–130 resamples the first block stored in its data memory 138–142 and calculates the coordinates and size of the next packet transfer to be executed. In the second step, the DSPs 124–130 compare the previous block (k−1) with the one just processed (k), while the transfer controller 134 fetches the next block (k+1) to bring it on-chip. When the DSPs 124–130 have processed all the blocks along the Z axis, the rendering for that particular block is done and the result is output for display.

The visualization process enables arbitrary rendering of a 128×128×128 volume at any viewing angle at a frame rate of approximately 21.7 Hz on a single MVP processor 102 using a nearest neighbor interpolation. Using bilinear interpolation, arbitray rendering of a 128×128×128 volume at any viewing angle is achieved on a singe MVP 102 at a frame rate of approximately 11.3 Hz. For multiple MVPS 102,104 the speed increases. Accordingly, the operator is able to visualize a target volume in real-time on an ultrasound diagnostic imaging system having a multiprocessor. The target volume can be rendered at any arbitrary viewing angle in real-time.

The visualization process also enables an operator to concurrently view a 2D image slice of the 3D image volume projection. In one portion of the display screen the 2D projection of the 3D target volume portion is projected. In another portion of the display, a 2D image slice of the displayed volume is viewed. During image construction the 2D image slice is the current image plane being scanned. During image visualization, the operator picks which slice of the target volume is viewed as the 2D slice. The operator can change the 2D slice to be any slice from any viewing angle. Thus, the 2D slice is any arbitrary slice of the reference volume, and thus, of the displayed target volume portion. One advantage of such concurrent viewing of a 2D slice is that a 2D slice is obtained from a view not ordinarily available by conventional image scanning. For example, the operator can indicate a slice from a view which, if generated in the first instance directly from an image scan, would be hard to obtain because of anatomical constraints. Such angle might direct the transducer too deep to obtain an image of desired resolution or may run though anatomical parts adversely impacting the scan results. By extracting the 2D image slice from the 3D reference volume, a desired viewing angle is obtained at a desired resolution.

Meritorious and Advantageous Effects

Although a preferred embodiment of the invention has been illustrated and described, various alternatives, modifications and equivalents may be used. Therefore, the foregoing description should not be taken as limiting the scope of the inventions which are defined by the appended claims.

What is claimed is:

1. A method of generating an ultrasound image of a three-dimensional target volume from a plurality of ultrasound data frames corresponding to a scan of the target volume, each frame comprising data for a plurality of sample points within an ultrasound image plane encompassing said plurality of sample points, the method comprising the steps of:

for a first frame of the plurality of frames and a corresponding first image plane, defining a first image plane coordinate system for the sample points of said first frame, the first image plane coordinate system having a first axis and a second axis orthogonal to the first axis;

defining a reference coordinate system having three orthogonal axes, in which a first reference coordinate system axis is parallel to the first axis of the first image plane coordinate system, a second reference coordinate system axis is parallel to the second axis of the first image plane coordinate system, and a third reference coordinate system axis is perpendicular to the first image plane, and wherein the first image plane occurs where a coordinate of the third reference coordinate system axis is zero;

for each i-th frame of the plurality of ultrasound data frames after the first frame, (i) identifying an i-th image plane coordinate system for the sample points of said i-th frame;

(ii) transposing i-th image plane coordinate system coordinates of each sample point in the i-th image plane into real-valued coordinates within the reference coordinate system;

(iii) for each one of a plurality of sample points within the i-th image plane interpolating a data value for the sample point to achieve an interpolated value for a discrete-valued coordinate of the reference coordinate system nearest to said sample point's real-valued reference coordinate system coordinate, and (iv) storing the achieved interpolated value in a memory location corresponding to the reference coordinate system discrete-valued coordinate; and outputting memory contents for the reference coordinate system discrete-valued coordinates to generate a display image projection of at least a three dimensional portion of the target volume.

2. The method of claim 1, further comprising after the step of defining the reference coordinate system, allocating first memory address space for storing data points for discrete coordinate positions for a rectilinear reference volume, the reference volume being defined within a first quadrant of the reference coordinate system, and wherein said steps of interpolating and storing are performed for each one sample point within the i-th image plane occurring within the reference volume, and wherein said memory location for said storing step is within said first memory address space.

3. The method of claim 2, in which the first memory address space is allocated to store achieved interpolated values along a given row of a given third reference coordinate system axis slice of the reference volume in sequential address locations, and wherein the first memory address space is further allocated to store achieved interpolated values for adjacent rows of the given third reference coordinate system axis slice in adjacent first memory address space.

4. The method of claim 1, further comprising the step of generating pixel data for the display image projection, the step of generating pixel data comprising for a given pixel the step of identifying reference coordinate system discrete-valued coordinates which overlap for the display image projection and using only one of the achieved interpolated values for the overlapping coordinates to derive the pixel data for the given pixel.

5. The method of claim 1, further comprising the step of generating a display image projection of at least a three dimensional portion of the target volume incrementally after the steps of transposing, interpolating and storing are performed for any i-th image plane.

6. The method of claim 5, in which an operator viewing the target volume portion is able to view gaps in the target volume portion where sample points were not obtained during scanning, and in response re-scanning a portion of the target volume to fill in the gaps.

7. The method of claim 1, wherein for each i-th frame of the plurality of ultrasound data frames, a position sensor senses position and orientation information, the position and orientation information for a given i-th frame being used in the transposing step for transposing the i-th image plane coordinate system coordinates into reference coordinate system coordinates.

8. The method of claim 1, wherein the display image projection of the portion of the target volume is for a first viewing direction of the target volume portion, and further comprising the step of generating a display image projection of the target volume portion for a second viewing direction different than the first viewing direction.

9. The method of claim 8, in which the step of generating comprises:

computing a translation offset for respective slices of the reference volume;

processing at a first processor a first rectangular portion of each one slice of a first plurality of slices within a first overlap region occurring for the second viewing direction, wherein size of the first rectangular portion varies for each one of the first plurality of slices;

processing at a second processor a second rectangular portion of each one slice of a second plurality of slices within a second overlap region occurring for the second viewing direction; and wherein the step of processing at a first processor comprises determining which stored achieved interpolated value corresponding to overlapping points on the display image projection of the first plurality of slices is displayed for the second viewing direction; and wherein the step of processing at a second processor comprises determining which stored achieved interpolated value corresponding to overlapping points on the display image projection of the second plurality of slices is displayed for the second viewing direction.

10. The method of claim 9, in which the first rectangular portion of said first plurality of slices comprises multiple row portions of each one slice of said first plurality of slices, each row portion of a said one slice corresponding to a contiguous portion of memory storing the achieved interpolated values for adjacent coordinates within a corresponding row of the reference coordinate system.

11. The method of claim 10, in which the first processor and second processor reside on a common integrated circuit, the common integrate circuit further comprising a transfer controller and on-chip memory, and wherein the transfer controller moves data corresponding to the first rectangular portions on-chip while the first processor processes data corresponding to a rectangular portion other than the first rectangular portion.

12. The method of claim 1, wherein the step of interpolating a data value for a sample point comprises interpolating the data value for said sample point to achieve an interpolated value for each one of a plurality of discrete-valued coordinates of the reference coordinate system nearest to said sample point's real-valued reference coordinate system coordinate.

13. A method of incrementally generating an ultrasound image of a three-dimensional target volume in real time from a sequence of ultrasound data frames corresponding to a scan of the target volume, each frame comprising data for a plurality of sample points within an ultrasound image plane encompassing said plurality of sample points, the method comprising the steps of:

for a first frame of the plurality of frames and a corresponding first image plane, defining a first image plane coordinate system for the sample points of said first frame, the first image plane coordinate system having a first axis and a second axis orthogonal to the first axis;

defining a reference coordinate system having three orthogonal axes, in which a first reference coordinate system axis is parallel to the first axis of the first image plane coordinate system, a second reference coordinate system axis is parallel to the second axis of the first image plane coordinate system, and a third reference coordinate system axis is perpendicular to the first image plane, and wherein the first image plane occurs where a coordinate of the third reference coordinate system axis is zero;

for each i-th frame of the plurality of ultrasound data frames after the first frame, (i) identifying an i-th image plane coordinate system for the sample points of said i-th frame, (ii) transposing i-th image plane coordinate system coordinates of each sample point in the i-th image plane into real-valued coordinates within the reference coordinate system, (iii) for each one of a plurality of sample points within the i-th image plane interpolating a data value for the sample point to achieve an interpolated value for a discrete-valued coordinate of the reference coordinate system nearest to said sample points real-valued reference coordinate system coordinate.

(iv) storing the achieved interpolated value in a memory location corresponding to the reference coordinate system discrete-valued coordinate; and (v) outputting memory contents for the reference coordinate system discrete-valued coordinates to generate a display image projection of at least a three dimensional portion of the target volume.

14. An ultrasound system for generating an ultrasound image of a three-dimensional target volume in real time from a plurality of ultrasound data frames corresponding to a scan of the target volume, each frame comprising data for a plurality of sample points within an ultrasound image plane encompassing said plurality of sample points, the system comprising:

a transducer array for transmitting ultrasound energy into a patient in the vicinity of the target volume and for receiving echoes of the ultrasound energy, the received echoes being transformed into the frames of ultrasound data;

a processing apparatus for processing the frames of ultrasound data to generate image data; and a display device for displaying an image projection of at least a three dimensional portion of the target volume, wherein the image projection is derived from the image data;

wherein for a first frame of the plurality of frames and a corresponding first image plane, the processing apparatus defines a first image plane coordinate system for the sample points of said first frame, the first image plane coordinate system having a first axis and a second axis orthogonal to the first axis;

wherein the processing apparatus defines a reference coordinate system having three orthogonal axes, in which a first reference coordinate system axis is parallel to the first axis of the first image plane coordinate system, a second reference coordinate system axis is parallel to the second axis of the first image plane coordinate system, and a third reference coordinate system axis is perpendicular to the first image plane, and wherein the first image plane occurs where a coordinate of the third reference coordinate system axis is zero;

wherein for each i-th frame of the plurality of ultrasound data frames after the first frame, the processing apparatus (i) identifies an i-th image plane coordinate system for the sample points of said i-th frame, (ii) transposes i-th image plane coordinate system coordinates of each sample point in the i-th image plane into real-valued coordinates within the reference coordinate system, (iii) for each one of a plurality of sample points within the i-th image plane, interpolates a data value for the sample point to achieve an interpolated value for a discrete-valued coordinate of the reference coordinate system nearest to said sample point's real-valued reference coordinate system coordinate, (iv) and stores the achieved interpolated value in a memory location corresponding to the reference coordinate system discrete-valued coordinate as image data.

15. The system of claim 14, further comprising first memory having an address space for storing data points for discrete coordinate positions for a rectilinear reference volume, the reference volume being defined within a first quadrant of the reference coordinate system, and wherein the processing apparatus interpolates and stores within the first memory for each one sample point within the i-th image plane occurring within the reference volume.

16. The system of claim 15, in which the first memory address space is allocated to store achieved interpolated values along a given row of a given third reference coordinate system axis slice of the reference volume in sequential address locations, and wherein the first memory address space is further allocated to store achieved interpolated values for adjacent rows of the given third reference coordinate system axis slice in adjacent first memory address space.

17. The system of claim 14, in which the processing apparatus generates pixel data for the display image projection by identifying reference coordinate system discrete-valued coordinates which overlap for the display image projection and using only one of the achieved interpolated values for the overlapping coordinates to derive the pixel data for the given pixel.

18. The system of claim 17, in which the target volume portion is constructed and displayed incrementally as respective frames of ultrasound data are processed by the processing apparatus.

19. The system of claim 14, in which a display image projection of at least a three dimensional portion of the target volume is generated and displayed incrementally after the processing apparatus transposes, interpolates, and stores for any i-th image plane.

20. The system of claim 14, wherein the display image projection of the portion of the target volume is for a first viewing direction of the target volume portion, and wherein the processing apparatus generates pixel data for a display image projection of the target volume portion for a second viewing direction different than the first viewing direction.

21. The system of claim 20, in which the processing apparatus comprises a multiprocessor integrated circuit having a first processor, a second processor, a transfer controller and on-chip memory;

the multiprocessor computing a translation offset for respective slices of the reference volume;

the first processor processing a first rectangular portion of each one slice of a first plurality of slices within a first overlap region occurring for the second viewing direction, wherein size of the first rectangular portion varies for each one of the first plurality of slices, and the first processor determining for each set of overlapping points on the display image projection of the first plurality of slices within the first rectangular portion, which stored achieved interpolated value is displayed for the second viewing direction;

the second processor concurrently processing a second rectangular portion of each one slice of a second plurality of slices within a second overlap region occurring for the second viewing direction, and the second processor determining for each set of overlapping points on the display image projection of the second plurality of slices within the second rectangular portion, which stored achieved interpolated value is displayed for the second viewing direction.

22. The system of claim 21, in which the first rectangular portion of said first plurality of slices comprises multiple row portions of each one slice of said first plurality of slices, each row portion of a said one slice corresponding to a contiguous portion of memory storing the achieved interpolated values for adjacent coordinates within a corresponding row of the reference coordinate system.

23. The system of claim 22, wherein the transfer controller moves data corresponding to the first rectangular portions on-chip while the first processor processes data corresponding to a rectangular portion other than the first rectangular portion.

* * * * *